United States Patent [19]
Fleche

[11] Patent Number: 5,981,742
[45] Date of Patent: Nov. 9, 1999

[54] GLUCURONYL ARABINARATES AND PROCESS FOR PRODUCING THEM

[75] Inventor: Guy Fleche, Hazebrouck, France

[73] Assignee: Roquette Freres, Lestrem, France

[21] Appl. No.: 08/769,052

[22] Filed: Dec. 18, 1996

[30] Foreign Application Priority Data

Dec. 21, 1995 [FR] France .................................. 95 15268

[51] Int. Cl.$^6$ ...................................................... C07H 1/00
[52] U.S. Cl. .................................. 536/123.1; 536/123.13; 536/124
[58] Field of Search ............................ 536/123.1, 123.13, 536/124

[56] References Cited

U.S. PATENT DOCUMENTS

| | | | |
|---|---|---|---|
| 2,587,906 | 3/1952 | Schmidt | 562/527 |
| 4,125,559 | 11/1978 | Scholz et al. | 562/531 |
| 4,618,675 | 10/1986 | Lichtenthaler et al. | 536/17.2 |
| 4,985,553 | 1/1991 | Fuertes et al. | 536/124 |

FOREIGN PATENT DOCUMENTS

| | | |
|---|---|---|
| 618 164 | 9/1935 | Germany . |
| WO 94/28030 | 12/1994 | WIPO . |
| WO 95/07303 | 3/1995 | WIPO . |

OTHER PUBLICATIONS

Food Sci. Technol. 1985, vol. 14, chap. 15, p. 286 (Kieboom and van Bekkum).
Carbohydrate Research. 214 (1991) 71–85 (Hendriks, Kuster and Marin).

*Primary Examiner*—Kathleen K. Fonda
*Attorney, Agent, or Firm*—Henderson & Sturm

[57] ABSTRACT

The invention related to glucuronyl arabinarates, to a process for producing these glucuronyl arabinarates consisting in carrying out the oxidative alkaline degradation of a starch hydrolysate so as to obtain firstly glucosyl arabinonates and then, by a selective oxidation of all or part of the primary alcohol functional groups of the glucosyl arabinonates to obtain the glucuronyl arabinarates, and to the use of the glucuronyl arabinarates as builders or co-builders in the formulation of detergent compositions.

10 Claims, No Drawings

GLUCURONYL ARABINARATES AND PROCESS FOR PRODUCING THEM

The subject of the present invention is, as new industrial products, glucuronyl arabinarates.

It also relates to a process for producing these products as well as their application as sequestering and dispersing agents in detergent compositions.

Other characteristics and advantages of the present invention will emerge on reading the description which follows.

The term glucuronyl arabinarates designates, in the present invention, not only glucuronyl-($\alpha$, 1-3)-arabinaric acid (or its salts), but also polyglucuronyl arabinarates, which are molecules of a polymeric nature consisting essentially of a chain of anhydroglucuronic units linked by a glycoside bond ($\alpha$, 1-4) and covalently linked by the same type of bond ($\alpha$, 1-3) to a terminal unit of arabinaric acid.

It will be stated later that glucuronyl-($\alpha$, 1-3)-arabinaric acid, composed of a glucuronyl unit and a terminal unit of arabinaric acid, has a DP (degree of polymerization) of 2. A glucuronylarabinaric acid composed of two glucuronyl units will have a DP of 3, and so on.

In the products of the invention, these glucuronyl units, also called anhydroglucuronic units, will be able to alternate frequently to a greater or lesser degree and repetitively to a greater or lesser degree, with anhydroglucoside units, also called glucosyl units, that is to say unoxidized units.

It is known that products can be obtained whose structure resembles those of the presert invention: polyglucuronyl glucarates, by the action of nitric acid on starch at low temperature (Food. Sci. Technol. 1985, vol 14, chap. 15, page 286, KIEBOOM and VAN BEKKUM). The polymers in question contain, in this case, about one anhydroglucuronyl unit for one anhydroglucosyl unit and in contrast to the products of the invention, their terminal unit consists of a glucaric acid.

Other polyglucuronyl glucarates containing more anhydroglucuronyl units relative to the anhydroglucosyl units can be obtained according to the teachings of International Patent Application WO 94/28030 by the action of nitrogen dioxide or tetroxide on starches or potato starches.

The polyglucuronyl glucarates in question may contain from 70 to 95% of anhydroglucuronyl units per 5 to 30% of anhydroglucosyl units.

Other polyglucuronyl glucarates containing at least 90% of anhydroglucuronyl units per 10% of anhydroglucosyl units may be obtained by the process described in International Patent Application Wo 95/07303. The process described in this patent application consists in oxidizing starch hydrolysates by the action of hypohalites in the presence of catalytic amounts of a binary or tertiary alkyl nitroxyl such as 2,2,6,6-tetramethylpiperidin-1-oxyl. This process is found, however, to be incapable of oxidizing the relatively heavy oligosaccharides (DP greater than 15) in their terminal hemiacetal or ketone functional group. This results in the fact that a substantial quantity of polyglucuronyl glucuronates of high DP persist in the polyglucuronyl glucarates of lower DP and that the products obtained are not stable in an alkaline medium or to heat.

Glucosyl arabinonates, products whose structure also resembles that of the products in accordance with the present invention, may be obtained by oxidative alkaline degradation of various disaccharides using air or oxygen.

Under these conditions, as is explained in German Patent DE 618,164, the maltose provides the glucosyl ($\alpha$, 1-3) arabinonate or, as is explained in American Patent U.S. Pat. No. 4,618,675, the palatinose provides the glucosyl ($\alpha$, 1-5) arabinonate.

It will have been understood that these products differ from the present invention in the fact that their terminal unit is an arabinonic acid and not an arabinaric acid. They also differ therefrom in the fact that the other constituent unit of the molecule is necessarily an anhydroglucosyl radical and not an anhydroglucuronyl radical. However, products according to the invention may also contain anhydroglucoside units since they also contain at least one anhydroglucuronyl unit and one terminal end of arabinaric acid.

Finally, other products, whose structure also resembles that of the products of the present invention, may be obtained by catalytic oxidation of starch hydrolysates using atmospheric oxygen and charcoal-bound noble metal-based catalysts, as is taught in patent U.S. Pat. No. 4,985,553 held by the applicant company.

The products obtained by this process are poly-glucosyl gluconates.

All these glucuronyl glucarates, glucosyl arabinonates and glucosyl gluconates of the prior art carry carboxylic functional groups and, to varying degrees, but in the same way as other carboxylic acids such as citric acid, gluconic acid or polyacrylic acids, exhibit sequestering properties which allow these products to play the role of "builders" or of "cobuilders" in detergent formulations.

However, none of them combines, on its own and to a sufficient degree, all of the following qualities:

high sequestering power,
high dispersing power,
high biodegradability,
high stability,
attractive price, which are those assigned to an ideal "builder" or "cobuilder".

In addition, the trend being for detergent compositions to become increasingly concentrated in products which are truly active: surfactants, enzymes, bleaching agents, there is increasingly no room for the "builder-cobuilder" system whose essential role can be reduced, after all, to correcting only the shortcomings of the washings and especially their alkaline-earth metal salt consent.

The need therefore existed to develop a product capable of serving as "builder" or as "cobuilder" in modern detergent compositions and which has simultaneously all the qualities mentioned above.

The applicant company has found that such a need could be satisfied by the glucuronyl arabinarates of the invention.

After numerous tests, the applicant company demonstrated:
that it was possible to industrially manufacture such products with inexpensive raw materials and processes;
that the sequestering and dispersing powers of these products were at such a level that their use in detergents resulted in very low redeposition levels and incrustation levels for the fabrics washed with these detergents;
that such products were easily biodegradable;
that such products were sufficiently stable to withstand both thermal stresses linked to the processes for drying the detergent compositions and the chemical stresses linked to the stability of the organic molecules in these highly alkaline detergent compositions.

On this latter point, the main disadvantage of the detergent compositions of oxidized starch hydrolysates according to the prior art, whether in the case of glucuronyl glucarates, glucosyl arabinonates or glucosyl gluconates, is the persistence, in these oxidized starch hydrolysates, of reducing hemiacetal ends which are unstable to heat and in alkaline medium.

Such a defect is of course unacceptable and manifests itself by a brown yellow colour in detergent powders or in liquid detergents, at best after a short period of storage, at worst as soon as they are formulated.

A specific process for producing the glucuronyl arabinarates according to the invention makes it possible, as will be seen later, to obtain products riot exhibiting this defect.

First of all, the present invention therefore relates, as new products, to glucuronyl arabinarates.

Preferably, it relates to the compositions of glucuronyl arabinarates having a mean degree of polymerization greater than or equal to 2.

More preferably, the products of the invention have a mean degree of polymerization of between 2 and 50 and still more preferably of between 2 and 10.

This is explained by the fact that the compositions of glucuronyl arabinarates according to the invention having the preferred mean DP values develop the highest sequestering powers.

According to the present invention, the preferred compositions of glucuronyl arabinarates are those which contain from 100% to 50% of anhydroglucuronyl units, preferably from 99% to 60% of anhydroglucuronyl units, this percentage of anhydroglucuronyl units being expressed relative to the sum of the anhydroglucuronyl and anhydroglucosyl units.

These preferences are explained by the fact that it is, on the one hand, difficult to completely oxidize all the primary alcohol functional groups of a polygLucan, of any type, and, on the other hand, by the fact that below the thresholds indicated, the sequestering and dispersing properties of the glucuronyl arabinarates are no longer manifested as satisfactorily in the use of these products in detergent formulations.

Whatever the case, the compositions according to the invention contain less than 1%, preferably less than 0.7%, and still more preferably less than 0.5% of free reducing sugars, expressed as free glucose equivalents and measured by the BERTRAND method.

The reason for these preferences is because above the indicated limits, these free reducing sugars, which show the presence of hemiacetal ends, would prove to be the cause of excessively marked phenomena of instability to heat and to the alkalinity of the detergent compositions into which the products of the invention would enter.

According to another aspect of the present invention, a process for producing the glucuronyl arabinarates in accordance with the invention consists:

in a first stage, in carrying out the oxidative alkaline degradation of a starch hydrolysate so as to obtain glucosyl arabinonates, in a second stage, in carrying out the selective oxidation of all or part of the primary alcohol functional groups of these glucosyl arabinonates.

In the present invention, the term glucosyl arabinonates covers glucosyl-($\alpha$, 1-3)-arabinonate but also the polyglucosyl arabinonates, that is to say molecules consisting of a chain of at least two anhydroglucoside units covalently linked to a terminal molecule of arabinonic acid.

Starch hydrolysate is intended by the applicant to designate here any of the starch or potato starch types which have been subjected to the action of acids or enzymes or both, so as to obtain therefrom solubility in water and reduction of the molecular mass. The dextrins, maltodextrins, glucose syrups and maltose syrups are therefore covered and more particularly those whose mean degree of polymerization corresponds to the mean degree of polymerization of the products of the invention which are preferred.

Oxidative alkaline degradation is intended to mean the processes which consist in subjecting aqueous solutions of oxidizable compounds to the action of air or oxygen finely divided in a highly alkaline medium. This oxidation may be catalysed by various promoters, for example methylene blue as indicated in American Patent U.S. Pat. No. 2,587,906 or by a redox couple consisting of anthraquinone-2-monosulphonic acid and of hydrogen peroxide (HENDRICKS, KUSTER and MARIN, Carb. res, 214 (1991) 71–85). This oxidation can take place at atmospheric pressure using air, or under pressure using oxygen as indicated in American Patent U.S. Pat. No. 4,125,559.

Although these reactions of oxidative alkaline degradation of the reducing sugars have always; been carried out on mono-or disaccharides such as especially glucose, mannose, fructose, maltose or lactose, the applicant observed that the teaching of the abovementioned documents could also be extended to polysaccharides endowed with a reducing power offered by a hemiacetal or ketone functional group.

This oxidative alkaline degradation reaction results in the formation, starting with the residue carrying this hemiacetal or ketone functional group, of a residue which has lost one carbon atom but which becomes a carrier of a carboxyl functional group.

Formic acid is formed concomitantly from this carbon atom removed from the residue carrying the reducing hemiacetal or ketone functional group.

In this first oxidative alkaline degradation stage according to the process in accordance with the invention, the various components of the starch hydrolysates, namely glucose, maltose, oligoglucosyl glucose and polyglucosyl glucose are therefore converted to arabinonate, glucosyl arabinonate, oligoglucosyl arabinonate and polyglucosyl arabinonate, respectively, with simultaneous formation of formate.

This alkaline oxidative degradation reaction producing at least two molecules of acid (one molecule of arabinonate or of glucosyl arabinonate and one molecule of formate) per molecule of reducing sugar used, it is necessary either to provide an alkaline reserve sufficient to bring the reaction to completion or to add the alkali as it is used up by the reaction.

Generally, it is advisable to use 2.1 to 3 mol and preferably from 2.2 to 2.4 mole of sodium hydroxide or of potassium hydroxide per mole of hemiacetal or ketone functional group to be oxidized, but other alkalis used in these same proportions may also be suitable.

The concentration of the starch hydrolysates subjected to this oxidation stage is of little importance provided that reactors equipped with efficient stirring and aeration means are available. However, the oxidative alkaline degradation stage will be preferably carried out on aqueous solutions of starch hydrolysate having a concentration of 10 to 60% and preferably of 25 to 40% dry matter.

This oxidation stage being highly exothermic, it is advisable to use reactors provided with an efficient cooling device. This oxidation stage is preferably carried out at a temperature of between 20 and 70° C. and preferably between 25 and 65° C.

It should be noted that as a general rule, the lowest temperatures make it possible to obtain the best selectivities but that this takes place at the expense of the speed of the reaction. In contrast, the highest temperatures make it possible to shorten the reaction times and may be used insofar as a slight depolymerization of the starch hydrolysate as well as the production of a few per cent of carbonic, oxalic, glyceric, glycclic, lactic, erythronic, metasaccharinic and dihydroxybutyric acids, and the like, are not damaging to the correct progress of the remainder of the process or to the use of the products obtained for the preparation of detergent compositions.

Whether the work is carried out in the presence of oxidation catalysts (methylene blue, anthraquinone-2-monosulphonic acid, hydrogen peroxide and the like) or not, it is preferable to allow the reaction to continue until a reducing sugar content, measured by the BERTRAND method, of between 0.1 and 2%, preferably of between 0.2 and 1%, is obtained, this content being expressed as percentage glucose equivalent weight relative to the dry matter content of the content of the reactor.

It will be noted that it would be unreasonable to prolong the reaction beyond this reducing sugar threshold since the next stage will further allow it to be reduced.

One of the main advantages of the process of the invention is in fact to provide products whose reducing sugar content is brought to a value which is so low that they practically no longer show any sensitivity to heat or to alkaline media and this even after prolonged periods of storage.

At the end of this oxidative alkaline degradation reaction, the catalyst is removed, if necessary, by percolation of the reaction medium on an activated charcoal column for example.

The second stage of the process according to the invention consists in selectively oxidizing all or part of the primary alcohol functional groups of the glucosyl arabinonates obtained at the preceding stage. It may be carried out in various ways.

There may be used, for example, oxidation processes using nitric acid, nitrogen dioxide or nitrogen tetroxide as already mentioned. However, these processes require neutralizing the excess alkali necessary for carrying out the first stage and they also require drying the product obtained after this first stage.

It is therefore preferable to carry out this oxidation of the primary alcohol functional groups by a method which is effective in alkaline medium and which can therefore take advantage of the excess alkali used during the first stage. Likewise, since it is preferable not to have to perform an intermediate drying of the glucosyl arabinonate, it is preferable to use a method which is effective on aqueous solutions of glucosyl arabinonates.

An oxidation method which is particularly preferred according to the process in accordance with the invention is that which is described in International Patent Application Wo 95/07303 and which allows the production of poly-α-glucuronic acids from inulin or starch hydrolysates.

In the process according to the invention, the glucosyl arabinonates obtained during the preceding stage are therefore subjected to the action of a hypohalite in the presence of a catalytic amount of a secondary or tertiary alkyl nitroxyl compound. Since this oxidation reaction occurs best at a pH of between 9 and 13, advantage is easily taken of the excess alkali necessary for carrying out the preceding oxidation stage.

As in the abovementioned patent application, 2,2,6,6-tetramethylpiperidin-1-oxyl designated hereinafter as TEMPO, is preferably used as oxidation catalyst.

In this oxidation reaction, the true oxidant is the nitrosonium cation which is reduced to hydroxyllmine when a primary alcohol functional group is oxidized to a carboxylic acid functional group. This nitrosonium cation is regenerated in situ by an oxidant which consists most conveniently of a hypochlorite/bromide pair. During the reaction, the pH is maintained constant by the addition of a base which is preferably the same as that which served during the first oxidation stage.

All or part of the anhydroglucosyl units of the glucosyl arabinonates are thus oxidized to anhydroglucuronyl units and the terminal arabinonic acid is thus oxidized to arabinaric acid.

This reaction for oxidation of the primary alcohol functional groups is carried out according to this patent application WO 95/07303 at a temperature of less than 30° C., preferably of between 0 and 5° C., and at a dry matter concentration of about 7 to 15 grams per liter of water, as is indicated in Patent Application WO 95/07303.

The applicant company has, however, observed that much higher concentrations and also higher temperatures ranging up to 50° C. could be used without any disadvantage, which results in smaller reactor volumes and the possibility of dispensing with the use of refrigerating units.

TEMPO is added in an amount of 0.1 to 2.5% by weight relative to the weight of glucosyl arabinonate to be oxidized to glucuronyl arabinarate.

The sodium hypochlorite is used in an amount of 2 mol per mole of primary alcohol to be oxidized.

In practice, it is preferable, nevertheless, to use up to 10% NaOCl in excess in relation to the reaction stoichiometry.

The sodium hypochlorite is therefore used taking this excess into account, preferably in an amount of 1.1 to 2.2 mol per mole of primary alcohol, according to the desired degree of oxidation which may vary from 50 to 100%.

As co-oxidant, sodium bromide may be added in an amount of 0.1 to 1 mole and preferably in an amount of 0.2 to 0.5 mol per mole of NaOCl used so as to accelerate the oxidation reaction.

The oxidation is generally complete after 1 hour. At this stage, the reducing sugar content of the reaction medium dropped further and became generally less than 0.5%, still more generally less than 0.2%.

The reaction medium is then extracted with ether, or better it is subjected to percolation on a granulated activated carbon column in order to remove the TEMPO.

After filtration of the purified reaction medium, it is generally concentrated to a dry matter content of 20% and then it is optionally dehydrated if it is desired that the products of the invention enter into the composition of detergents provided in powder form. Such a dehydration is obviously not necessary insofar as it is desired to formulate liquid detergents.

It is also possible, if desired, after concentration but before drying, to remove the sodium chloride which forms during the second stage of the process as well as the sodium bromide which was optionally added as co-oxidant, by techniques known to a person skilled in the art, such as ion exclusion chromatography on strong cationic resins.

The example which follows is intended to illustrate the invention and to allow it to be better understood.

EXAMPLE 1

1st stage: Oxidative Alkaline Degradation of a Starch Hydrolysate 2995 grams of water and 1591 grams of sodium hydroxide are introduced into a fermenter with a glass tank of BIOLAFITTE brand, having a working capacity of 20 liters, so as to form 4586 grams of caustic soda at 34.7%.

55 grams of sodium anthraquinone-2-monosulphonate and 18.2 ml of hydrogen peroxide at 110 volumes are then added to the caustic soda.

The fermenter is then aerated with an air flow rate of 20 liters per minute and while stirring at a speed of 1000 revolutions per minute.

After having stirred this mixture at 250° C. for 30 minutes, the temperature is raised to 45° C. 18.344 grams of a glucose syrup obtained by acid hydrolysis of maize starch, having a dry matter content of 50% and a DE of 37 (that is to say a mean degree of polymer-ization equal to 2.7) are then slowly added uniformly, over 3 hours 30 minutes.

The temperature is then set at 55° C. and the stirring and aeration are continued for 2 hours 30 minutes. The reducing sugar content of the reaction medium is then reduced to 0.3 g/100 g of dry matter content of glucose syrup. (It was initially 37 g/100 g).

The reaction medium is then percolated on a granular activated charcoal column so as to remove the sodium salt of anthraquinone-2-monosulphonic acid.

2nd stage: Selective Oxidation of the Primary Alcohol Functional Groups of Glycosyl Arabinonate 1146 grams of the solution obtained in the preceding stage (which corresponds to 459 g of dry matter content of glucose syrup used in the preceding stage) are added to a stirred tank with a total volume of 35 liters containing 8 liters of water and the mixture is cooled to 5° C.

42.7 grams of sodium bromide and 4.17 grams of TEMPO are then added. After leaving these ingredients to dissolve, which take a few minutes, 2.9 liters of a sodium hypochlorite solution at 157 g/l (javel water at 48° chlorometric) previously diluted to 25% and adjusted to pH 10.4 with hydrochloric acid are added all at once.

The temperature is then maintained at 5° C. by addition of a small amount of ice and the pH at 10.4 by continuous addition of 10% sodium hydroxide.

After 60 minutes, the consumption of sodium hydroxide became zero, indicating the end of the reaction.

The TEMPO is then removed by percolation of the reaction medium on a granular activated charcoal column and then the purified reaction medium is concentrated, after having been filtered, to a concentration of 20% dry matter.

The crude glucuronyl arabinarate thus obtained showed the following analysis, the percentages being expressed on the dry matter content of the concentrated reaction medium:

| | |
|---|---|
| Degradation products | 1% |
| (oxalate, glycerate, glycolate, lactate and the like) | |
| Active substance | 39.6% |
| (glucuronyl arabinarates) | |
| NaCl | 51.5% |
| NaBr | 3.1% |
| Formate | 4.8% |
| Sodium carboxylate level | 17.5% |
| (in weight % active substance) | |
| that is to say a conversion rate close to 100% | |
| Reducing sugar level | |
| (over total dry matter) | 0.15% |
| (over active substance) | 0.38% |
| Mean degree of polymerization (DP) | 2.7 |
| of the active substance | |

EXAMPLE 2

The product obtained in Example 1 is enriched with active substances by an ion exclusion chromatography technique on strong cationic resins.

A product titrating not more than 5% sodium chloride was thus obtained, which was spray-dried in order to obtain a white powder.

This powder was used as a substitute for the polyacrylates in a detergent formula in an amount of 1 part of glucuronyl arabinarates thus enriched per 1 part of polyacrylates.

Not only do the powders obtained not become coloured during storage, but they also exhibit very advantageous detergent qualities since after carrying out 25 consecutive washes of samples of cotton and cotton/polyester fabrics, the whiteness values obtained are found to be greater than the control polyacrylate.

In addition, the level of organic incrustations is found to be significantly lower.

I claim:

1. A compound which is either (a) glucuronyl-($\alpha$, 1-3)-arabinaric acid, (b) a salt of glucuronyl-($\alpha$, 1-3)-arabinaric acid, (c) a polymer consisting essentially of a chain of anhydroglucuronyl units linked by $\alpha$, 1–4 glycosidic bonds, which chain is linked by an ($\alpha$, 1-3) glycosidic bond to a terminal unit of arabinaric acid, (d) a polymer as in (c) wherein some but not all of the anhydroglucuronyl units are replaced with anhydroglucosyl units, or (e) a salt of a polymer as in (c) or (d).

2. A composition comprising two or more of the compounds of claim 1.

3. A composition of claim 2 containing from 100% to 50% of anhydroglucuronyl units, based on the total number of anhydroglucuronyl and anhydroglucosyl units.

4. A composition of claim 2 having a mean degree of polymerization between 2 and 50.

5. A composition of claim 4 having a mean degree of polymerization between 2 and 10.

6. A composition of claim 2 containing less than 1% of free reducing sugars, expressed as free glucose equivalents.

7. A process for manufacture of a composition of claim 2, wherein:

in a first stage, an oxidative alkaline degradation of a starch hydrolysate is carried out so as to obtain glucosyl arabinonates, and in a second stage, a selective oxidation of all or part of the primary alcohol functional groups of the glucosyl arabinonates obtained in the first stage is carried out.

8. The process according to claim 7, wherein the selective oxidation in the second stage is carried out by action of a hypohalite in the presence of a catalytic amount of a secondary or tertiary alkyl nitroxyl compound.

9. The process according to claim 8, wherein the secondary or tertiary alkyl nitroxyl compound is 2,2,6,6,-tetramethylpiperidin-1-oxyl (TEMPO).

10. The process according to claim 9, wherein the hypohalite used is sodium hypochlorite in an amount of 1.1 to 2.2 moles per mole of primary alcohol to be oxidized.

* * * * *